(12) United States Patent
Miyagi et al.

(10) Patent No.: US 6,492,542 B2
(45) Date of Patent: Dec. 10, 2002

(54) METHOD FOR PRODUCING CARBOXYLIC ACID TERTIARY ALKYL ESTER

(75) Inventors: Sachiko Miyagi, Wakayama (JP); Masayuki Maeda, Wakayama (JP); Seiji Kawano, Wakayama (JP); Taiichi Shiomi, Wakayama (JP)

(73) Assignee: Honshu Chemical Industry Co., Ltd., Wakayama (JP)

( * ) Notice: Subject to any disclaimer, the term of this patent is extended or adjusted under 35 U.S.C. 154(b) by 0 days.

(21) Appl. No.: 09/934,238

(22) Filed: Aug. 21, 2001

(65) Prior Publication Data

US 2002/0055649 A1 May 9, 2002

(30) Foreign Application Priority Data

Aug. 22, 2000 (JP) ........................................ 2000-250642
Aug. 9, 2001 (JP) ........................................ 2001-241503
Aug. 9, 2001 (JP) ........................................ 2001-241511

(51) Int. Cl.$^7$ .......................... C07C 69/76; C07C 69/74; C07C 69/02; C07C 309/00
(52) U.S. Cl. ........................ 560/100; 560/101; 560/102; 560/103; 560/128; 560/231; 560/562; 560/828
(58) Field of Search ................................ 560/128, 231, 560/100, 101, 102, 103; 562/828

(56) References Cited

PUBLICATIONS

"Dehydrations with Aromatic Sulfonyl Halides in Pyridine. A Convenient Method for the Preparation of Esters" Brewster et al. J. Am. Chem. Soc. vol. 77. pp. 6214–6215 (1955).*
"Convenient Preparation of Esters of Testosterone and 19–Norethisterone with Hindered Acids" Gunatilaka et al. J. Chem. Soc. Chem. Comm. pp. 980–981 (1978).*
"Esterification of Carboxylic Acids with Alcohols Using Benzenesulfonyl and Methanesulfonyl Chlorides" Dharmaratne et al. Ind. J. Chem. vol. 21B. pp. 39–41 (1981).*
Faith, Keyes, and Clark's Industrial Chemicals, 4$^{th}$ Ed. pp. 173–177. (1975).*

* cited by examiner

*Primary Examiner*—Mukund J. Shah
*Assistant Examiner*—Zachary C. Tucker
(74) *Attorney, Agent, or Firm*—Knobbe, Martens, Olson & Bear LLP

(57) ABSTRACT

A carboxylic acid tertiary alkyl ester (Chemical formula 1) of high purity is obtained at a high yield ratio, by continually adding an esterification agent possessing a monovalent acid group, which agent is ester-interchangeable with a tertiary alcohol, to a mixed fluid of a carboxylic acid and a tertiary alcohol:

$$R_1(COOR_2)_n. \qquad (1)$$

4 Claims, No Drawings

METHOD FOR PRODUCING CARBOXYLIC ACID TERTIARY ALKYL ESTER

BACKGROUND OF THE INVENTION

1. Field of the Invention

The present invention relates to a carboxylic acid tertiary alkyl ester, specifically, a monocarboxylic acid tertiary alkyl ester and a dicarboxylic acid tertiary alkyl ester. It relates to a method for producing, for example, t-butoxycarbonyl substituted norbornene derivatives or decahydronaphthalene-2,6-dicarboxylic acid di-t-butyl esters, etc. easily on an industrial scale at a good yield ratio. Furthermore, in detail, the present invention relates to a method for producing a monocarboxylic acid monoester or a dicarboxylic acid diester of a tertiary alcohol, whose production is generally difficult, from a corresponding monocarboxylic acid or dicarboxylic acid and a tertiary alcohol in a single-step reaction process and at a high yield ratio.

2. Description of the Related Art

Conventionally, it is known that an esterification reaction of a carboxylic acid and an alcohol can be prepared by a method of direct esterification in the presence of an acid catalyst, a method for making a carboxylic acid react with an alcohol after halogenating it, or a method for interchanging an ester in the presence of an acidic catalyst or a basic catalyst. These esterification reactions easily proceed with a primary or secondary alcohol. With a tertiary alcohol, however, an esterification reaction does not proceed well due to steric hindrance caused by substituents. Because a dissociation reaction of an ester generated can easily occur due to unstable carbocations, the esterification does not proceed easily using esterification methods usually used; it is difficult, and the yield ratio is extremely low.

In recent years, carboxylic acid tert-alkyl esters attract attention in the electronic materials field. For example, tetracyclo[4,4,0,1$^{2,5}$,1$^{7,10}$]dodece-8-ene-3-carboxylic acid t-butyl esters of a t-butoxycarbonyl substituted tetracyclododecen class attract attention as a material for highly integrated circuits, particularly for a resist resin suitable for exposure in a vacuum ultraviolet ray region for ArF excimer lasers, etc.

Conventionally, as a method for producing a t-butoxycarbonyl substituted tetracyclododecen class, it is known that it can be obtained by the Diels-Alder reaction of a t-butylacrylate and a dicyclopentadiene class (K. D. Ahn J. Photopolym. Sci. Technol., Vol. 11, No.3, 499–503 (1998)).

Unlike a case where a t-butoxycarbonyl substituted norbornane class can be obtained easily at a high yield by the Diels-Alder reaction of a t-butylacrylate and a cyclopentadiene class, the above-mentioned production method using a t-butylacrylate as a raw material includes a problem in that the Diels-Alder reaction requires the conditions of a high reaction temperature of 180 to 200° C. while applying pressure. For this reason, a carboxylic acid substituted tetracyclododecen class, which is generated with a butyl group being separated from a t-butoxycarbonyl substituted tetracyclododecen class generated from the reaction, is easily generated and there are cases where this can cause a side reaction. There are other problems that the yield ratio is low due to various by-products of a t-butoxycarbonyl substituted norbornane class generated and that precision distillation is required to obtain an object of high purity from a reaction product.

SUMMARY OF THE INVENTION

Consequently, in view of difficulties in producing carboxylic acid tertiary alkyl esters, e.g., the situation described above regarding the method for producing a t-butoxycarbonyl substituted tetracyclododecen class, an object of the present invention is to provide a method for producing carboxylic acid tertiary alkyl esters of high purity using a tertiary alcohol and carboxylic acids as raw materials, under conditions that are easily implemented on an industrial scale, at a high yield. Carboxylic acid tertiary alkyl esters here include monocarboxylic acid tertiary alkyl esters such as a t-butoxycarbonyl substituted tetracyclododecen class and a t-butoxycarbonyl substituted bicyclo-hept-ene and dicarboxylic acid di-tertiary alkyl esters such as decahydronaphthalene-2,6-dicarboxylic acid di-t-butyl esters.

According to the present invention, a method for producing a carboxylic acid tertiary alkyl ester expressed by chemical formula 1 is provided. The method is characterized in that an esterification agent possessing a monovalent acid group that is ester-interchangeable with a tertiary alcohol is added continually to a mixed fluid of a carboxylic acid and a tertiary alcohol in the presence of a catalyst.

[Chemical formula 1]

wherein $R_1$ indicates a hydrocarbon group; $R_2$ indicates a tertiary saturated hydrocarbon group; n indicates a positive integer 1 or 2.

DETAILED DESCRIPTION OF THE PREFERRED EMBODIMENT

As a carboxylic acid, a starting material, used in the production method according to the present invention, a hydrocarbon carboxylic acid that is a bridge-ring hydrocarbon monocarboxylic acid, e.g., a tetracyclododecen-ring or a norbornane-ring hydrocarbon monocarboxylic acid, can be used. These bridge-ring hydrocarbon monocarboxylic acids include: monocarboxylic acids such as tetracyclo[4,4,0,1$^{2,5}$, 1$^{7,10}$]dodece-8-ene-3-carboxylic acid, tetracyclo[4,4,0,1$^{2,5}$, 1$^{7,10}$]dodece-8-ene-3-methyl-3-carboxylic acid and bicyclo[2,2,1]hept-5-ene-2-methyl-2-carboxylic acid, or dicarboxylic acids such as tetracyclo[4,4,0,1$^{2,5}$,1$^{7,10}$]dodece-8-ene-2, 3-dicarboxylic acid and bicyclo[2,2,1]hept-5-ene-2,3-dicarboxylic acid.

Likewise, aromatic-ring hydrocarbon carboxylic acids such as phenyl-ring, biphenyl-ring, naphthalene-ring, anthracene-ring hydrocarbon carboxylic acids, can also be mentioned. These aromatic-ring hydrocarbon carboxylic acids include: monocarboxylic acids such as benzoic acid, P-isopropyl benzoic acid, methyl benzoic acid, 3-biphenyl carboxylic acid, α-naphthoic acid, β-naphthoic acid, 2-methyl-1-naphthoic acid, anthracene-2-carboxylic acid or, dicarboxylic acids such as isophthalic acid, terephthalic acid, naphthalene-1,4-dicarboxylic acid, naphthalene-1,5-dicarboxylic acid, and anthracene-1,3-dicarboxylic acid.

Additionally, alicyclic hydrocarbon carboxylic acids such as cyclohexane-ring, bicyclohexane-ring, cyclonaphthalene-ring, tricyclo[5,2,1,0$^{2,6}$]decane-ring, spiro[4,5]decane-ring hydrocarbon carboxylic acids can be used. These alicyclic hydrocarbon carboxylic acids include: monocarboxylic acids such as cyclohexane carboxylic acid, 2-methylcyclohexane carboxylic acid, spiro[4,5]decane-1-carboxylic acid, hydrindene-1-carboxylic acid, decalin-1-carboxylic acid, etc., or dicarboxylic acids such as cyclohexane-1,2-dicarboxylic acid, cyclohexane-1,4-dicarboxylic acid, decahydronaphthalene-2,6-dicarboxylic acid, spiro[3,3]heptane-2,6-dicarboxylic acid, bicyclohexyl-2,2'-dicarboxylic acid, etc.

Furthermore, carboxylic acids of aliphatic saturated hydrocarbon with 2 to 12 carbons, e.g., monocarboxylic acids such as acetic acid, propionic acid, butyric acid, valerianic acid, lauric acid and stearic acid, or dicarboxylic acids such as oxalic acid, malonic acid, succinic acid, adipic acid and sebacic acid, can be used.

As a tertiary alcohol used in the production method according to the present invention, fatty saturated tertiary alcohol, specifically aliphatic tertiary alcohols such as t-butyl alcohol, t-pentyl alcohol, t-hexyl alcohol, and 1,1,3,3-tetramethylbutyl alcohol, alicyclic tertiary alcohols such as 1-methyl-1-cyclohexyl alcohol, 1-ethyl-1-cyclohexyl alcohol, 1-methylethyl-1-cyclohexyl alcohol, 1-methylethyl-1-(4-isopropylcyclohexyl)alcohol, and bridge-ring tertiary alcohols such as 1-adamanthyl alcohol, 2-methyl-2-adamanthyl alcohol, can be used.

Consequently, as a carboxylic acid tert-alkyl ester, an object of the present invention expressed by the chemical formula 1, monocarboxylic acid tert-alkyl esters specifically include: tetracyclo[4,4,0,1$^{2,5}$,1$^{7,10}$]dodece-8-ene-3-carboxylic acid-t-butyl esters, tetracyclo[4,4,0,1$^{2,5}$,1$^{7,10}$]dodece-8-ene-3-methyl-3-carboxylic acid-t-butyl esters, bicyclo[2,2,1]hept-5-ene-2-methyl-2-carboxylic acid-t-butyl esters, tetracyclo[4,4,0,1$^{2,5}$,1$^{7,10}$]dodece-8-ene-3-carboxylic acid-t-pentyl esters, tetracyclo[4,4,0,1$^{2,5}$,1$^{7,10}$]dodece-8-ene-3-methyl-3-carboxylic acid-t-pentyl esters, bicyclo[2,2,1]hept-5-ene-2-carboxylic acid-t-pentyl esters, bicyclo[2,2,1]hept-5-ene-2-methyl-2-carboxylic acid-t-pentyl esters, tetracyclo[4,4,0,1$^{2,5}$,1$^{7,10}$]dodece-8-ene-3-carboxylic acid-t-1-ethylcyclohexyl esters, tetracyclo[4,4,0,1$^{2,5}$,1$^{7,10}$]dodece-8-ene-3-methyl-3-carboxylic acid-t-1-ethylcyclohexyl esters, bicyclo[2,2,1 ]hept-5-ene-2-carboxylic acid-t-1-ethylcyclohexyl esters, tetracyclo[4,4,0,1$^{2,5}$,1$^{7,10}$]dodece-8-ene-3-carboxylic acid-1-adamanthyl esters, bicyclo[2,2,1]hept-5-ene-2-methyl-2-carboxylic acid-t-1-ethylcyclohexyl esters, tetracyclo[4,4,0,1$^{2,5}$,1$^{7,10}$]dodece-8-ene-3-methyl-3-carboxylic acid-1-adamanthyl esters, bicyclo[2,2,1]hept-5-ene-2-carboxylic acid-1-adamanthyl esters, bicyclo[2,2,1]hept-5-ene-2-methyl-2-carboxylic acid-1-adamanthyl esters, benzoic acid-t-butyl esters, naphthalene2-carboxylic acid t-butyl esters, 3-biphenyl carboxylic acid t-butyl esters, cyclohexane carboxylic acid t-butyl esters, acetic acid t-butyl esters, propionic acid t-butyl esters, lauric acid t-butyl esters, and others.

As carboxylic acid tert-alkyl esters expressed by chemical formula 1 according to the present invention, dicarboxylic acid di-tert-alkyl esters specifically include: tetracyclo[4,4,0,1$^{2,5}$,1$^{7,10}$]dodece-8-ene-2,3-dicarboxylic acid-di-t-butyl esters, bicyclo[2,2,1]hept-5-ene-2,3-dicarboxylic acid-di-t-butyl esters, isophthalic acid di-t-butyl esters, naphthatlene-1,4-dicarboxylic acid di-t-butyl esters, decahydronaphthalene-2,6-di-t-butyl esters, decahydronaphthalene-2,6-dicycloheptyl esters and others.

In a method for producing a carboxylic acid tertiary alkyl ester expressed by chemical formula 1 according to the present invention, by continually adding an esterification agent possessing a monovalent acid group, which agent is ester-interchangeable with a tertiary alcohol, to a mixed fluid of a carboxylic acid and a tertiary alcohol in the presence of a catalyst, the carboxylic acid tertiary alkyl ester expressed by the chemical formula 1, which is an object of the present invention, can be obtained at a high yield ratio.

In the production method according to the present invention, a reaction is caused by continually adding an esterification agent possessing a monovalent acid group, which agent is ester-interchangeable with a tertiary alcohol, to a mixed fluid of a carboxylic acid and a tertiary alcohol.

As a method for continuously adding the esterification agent, the esterification agent is added to a mixed fluid of a carboxylic acid and a tertiary alcohol continuously or regularly (by dividing it into smaller portions) over a period of time from 5 to 10 hours.

The reactions in the method can be determined as follows: As shown in chemical formula 3 below, a reaction that is supposed to be a main reaction of the present invention includes, first, the esterification agent possessing a monovalent acid group, which agent is ester-interchangeable with a tertiary alcohol expressed by chemical formula 2, for example, and acts on a carboxylic acid that is a raw material, and then an ester compound possessing a monovalent acid group, which compound is ester-interchangeable with a tertiary alcohol, is generated.

$$X\text{—}SO_2Ar \qquad (2)$$

wherein X indicates a halogen atom; Ar indicates a benzene ring or an alkyl-substituted benzene ring of one to three carbons.

In this case, under reaction conditions according to the present invention, the ester compound expressed by above-mentioned formula 2 hardly reacts on a tertiary alcohol coexisting in the mixed fluid. The ester compound generated and the tertiary alcohol coexisting in the mixed fluid, which is another raw material, then react on each other to cause a transesterification. Because these two reactions selectively simultaneously proceed, in a non-equilibrium manner, it is supposed that the object of the present invention, i.e., a carboxylic acid tertiary alkyl ester expressed by chemical formula 1, is obtained at a high yield ratio in a seemingly single process:

(3)

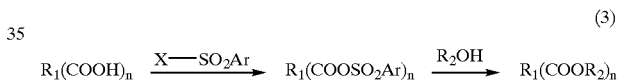

$$R_1(COOH)_n \xrightarrow{X\text{—}SO_2Ar} R_1(COOSO_2Ar)_n \xrightarrow{R_2OH} R_1(COOR_2)_n$$

wherein $R_1$ and $R_2$ are the same as those used in the chemical formula 1; X and Ar are the same as those used in chemical formula 2.

In the production method according to the present invention, a purified carboxylic acid can be used, but a carboxylic acid of 95% purity is preferable.

In the production method according to the present invention, it is preferable that a reaction take place in the presence of a specific catalyst.

As a catalyst used, tertiary amides are preferable. For example, dimethylacetamide (DMAC), dimethylformamide (DMF), diethylacetamide, diethylformamide, N-methylpyrrolidone, etc. can be used as examples. Among them, dimethylacetamide (DMAC) and dimethylformamide (DMF) are preferable, and dimethylacetamide is particularly preferable. An amount used should be approximately within a range of 0.01 to 30 parts by weight, preferably within a range of 0.1 to 5 parts by weight, to a carboxylic acid.

In the production method according to the present invention, as an esterification agent possessing a monovalent acid group, which agent is ester-interchangeable with a tertiary alcohol, an esterification agent that possesses an acid group in, for example, a sulfonyl group, an acetyl group or a trifluoroacetyl group can be used. Specifically, an aromatic sulfonyl halide, an acetic anhydride or a trifluoroacetic anhydride, which is expressed by chemical formula 2 below can be used, including aliphatic sulfonylchlorides such as methanesulfonylchloride and aromatic sulfonylchlorides such as P-toluenesulfonic acid. Among them, an aromatic sulfonyl halide, which is expressed by chemical formula 2 below, is preferable. P-toluenesulfonic acid is particularly preferable.

An amount of the esterification agent used is normally 100 to 500 mole %, preferably 100 to 200 mole % if a monocarboxylic acid is used as a raw material. If a dicarboxylic acid is used as a raw material, an amount to be used is 200 to 1000 mole %, preferable 200–400 mole %.

In the production method according to the present invention, at the time of an esterification reaction, to complement acids generating from the esterification agent possessing a monovalent acid group, which agent is ester-interchangeable with a tertiary alcohol, a base is used. The base used is not particularly limited, but triethylamine, pyridyne, calcium carbonate, etc. can be used as examples. Among them, pyridyne is preferable.

The amount of a base to be used is within a range of 2.0 to 50 times by mole that of carboxylic acid, preferably within a range of 2.0 to 30 times by mole, in the case of monocarboxylic acid. In the case of dicarboxylic acid, the amount is within a range of 4.0 to 50 times by mole, preferably, within a range of 4.0 to 30 times by mole.

A reaction temperature is within a range of 30 to 80° C., preferably within a range of 40 to 60° C.

There is no restriction on the reaction pressure, but normally a reaction pressure is within a range of 100 to 1000 kPa, preferably within a range of 100 to 300 kPa. Under these reaction conditions, a reaction normally is normally completed in 1 to 20 hours.

Additionally, an end point of the esterification reaction can be confirmed by liquid chromatography (HPLC) analysis or gas chromatography analysis, etc.

In the production method according to the present invention, an esterification agent is added continually to a mixed fluid of a carboxylic acid and a tertiary alcohol using a method such as a dropping method at a temperature between 40 to 60° C., and further they are made to react. In this case, a catalyst such as dimethylacetamide, etc. can be added entirely in either of a mixed fluid of a carboxylic acid and a tertiary alcohol or the esterification agent, or in both by dividing the amount. In the present invention, a yield ratio of the target compound to the raw material carboxylic acid may be in the ranged of 40–90 mol %.

In the production method according to the present invention, at the time of the reaction, a solvent can be used as well. As a solvent, an organic solvent other than an alcohol is preferable. Aromatic solvents such as toluene, ketone solvents, ether solvents, etc. can be used. Additionally, a catalyst such as dimethylacetamide or a base such as pyridine, which are mentioned above, can be used as a solvent as well.

In the production method according to the present invention, after the reaction is completed, a reaction mixture is neutralized by an alkali aqueous solution such as sodium hydroxide. After removing a water layer by separating the mixture into two liquids, a refined carboxylic acid tertiary alkyl ester such as t-butoxycarbonyl-tetracyclododecen or decahydronaphthalene-2,6-di-t-butyl ester, which is an object of the present invention, can be obtained by removing the solvent in a remaining oil layer by distillation or other means.

The production method according to the present invention is described in further detail using embodiments.

Purity and the yield ratio of objects obtained in the embodiments were calculated by gas chromatography analysis or liquid chromatography (HPLC) analysis. The objects obtained were identified by mass spectrometric analysis and proton NMR analysis.

[Embodiment 1]
Producing Norbornane Carboxylic Acid t-butyl Ester
[Chemical Formula 4]

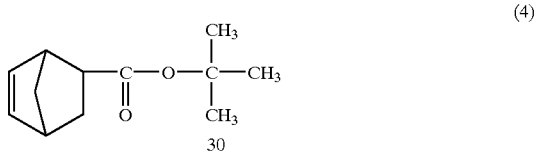

(4)

In a 1-liter four-opening flask equipped with a stirrer, a thermometer, a dropping funnel and a reflux condenser, 69 g (0.5 mol) of bicyclo(2,2,1)hept-5-ene-2 carboxylic acid and 118.5 g (1.5 mol) of pyridine, and 74 g (1.0 mol) of t-butanol were prepared. After replacing gas inside the flask with nitrogen gas, the temperature was raised to 60° C. and the starting materials were stirred and dissolved.

While maintaining the same temperature, a solution, in which p-toluenesulfonylchloride of 190 g (1.0 mol.) was dissolved in 204 g of dimethylacetamide, was added drop by drop for 1.5 hours, and then this mixture was stirred at the same temperature for two hours. After the reaction was complete, 204 g of toluene and 204 g of water were added to a reaction mixture obtained. After stirring it, a water layer was removed by separating the mixture into two liquids. 102 g of a 16% NaOH aqueous solution was added to the remaining oil layer. After stirring it upon further adding water, the water layer was removed by separating it into two liquids. By removing toluene, etc. contained in an oil layer obtained by vacuum distillation, the target compound, 78 g of bicyclo(2,2,1)hept-5-ene-2-carboxylic acid-t-butyl ester, was obtained as a slightly yellow liquid with 99.5% purity (by gas chromatography analysis). (A yield ratio of the target compound to the raw material carboxylic acid was 80%.)

[Embodiment 2]
Producing Tetracyclododecen Carboxylic Acid t-butyl Ester
[Chemical Formula 5]

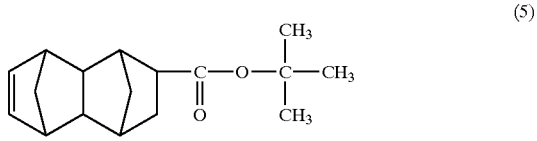

(5)

In a 2-liter four-opening flask equipped with a stirrer, a thermometer, a dropping funnel and a reflux condenser, 102 g (0.5 mol) of tetracyclo[4,4,0,1$^{2,5}$,1$^{7,10}$]dodece-8-en-3-carboxylic acid and 118.5 g (1.5 mol) of pyridine, and 74 g (1.0 mol) of t-butanol were prepared. After replacing gas inside the flask with nitrogen gas, the temperature was raised to 60° C. and the starting materials were stirred and dissolved.

While maintaining the same temperature, a solution, in which 190 g (1.0 mol.) of p-toluenesulfonylchloride was dissolved in 204 g of dimethylacetamide, was added drop by drop for 1.5 hours, and then this mixture was stirred at the same temperature for two hours. After the reaction was complete, 204 g of toluene and 204 g of water were added to the reaction mixture obtained. After stirring it for one hour, a water layer was removed by separating the mixture into two liquids.

102 g of a 16% NaOH aqueous solution was added to the remaining oil layer. After stirring it upon further adding water, the water layer was removed by separating it into two liquids. By removing toluene, etc. contained in an oil layer obtained by vacuum distillation, the target compound, 111 g of tetracyclo[4,4,0,1$^{2,5}$,1$^{7,10}$]dodece-8-ene-3-carboxylic acid t-butyl ester, was obtained as a slightly yellow liquid with 99.3% purity (by gas chromatography analysis). (A yield ratio of the target compound to the raw material carboxylic acid was 85%.)

[Embodiment 3]
Producing Norbornane Carboxylic Acid-ethylcyclohexyl Ester [Chemical Formula 6]

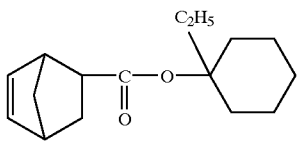

(6)

In a 2-liter four-opening flask equipped with a stirrer, a thermometer, a dropping funnel and a reflux condenser, 193.7 g (1.4 mol) of bicyclo(2,2,1)hept-5-ene-2 carboxylic acid and 215 g (1.68 mol) of 1-ethylcyclohexanol, and 58 g of N,N-dimethylacetamide were prepared. After replacing gas inside the flask with nitrogen gas, the temperature was raised to 55° C. and the starting materials were stirred and dissolved.

While maintaining the same temperature, a solution, in which 320.4 g (1.68 mol) of p-toluenesulfonylchloride was dissolved in 320 g of pyridine, was added drop by drop for 3 hours, and then this mixture was stirred at the same temperature for a night. After the reaction was complete, 580 g of toluene and 590 g of water were added to the reaction mixture obtained. After stirring it, a water layer was removed by separating the mixture into two liquids.

420 g of a 16% NaOH aqueous solution was added to the remaining oil layer. After stirring it upon further adding water, the water layer was removed by separating it into two liquids. By removing toluene, etc. contained in an oil layer obtained by vacuum distillation, the target compound, 243 g of bicyclo[2,2,1]hept-5-ene-2-carboxylic acid-1-ethylcyclohexyl ester, was obtained as a slightly yellow liquid with 98.8% purity (by liquid chromatography analysis). (A yield ratio of the target compound to the raw material carboxylic acid was 68.1%.)

[Embodiment 4]
Producing Norbornane Carboxylic Acid-t-pentyl Ester [Chemical Formula 7]

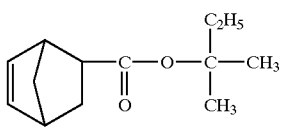

(7)

In a 5-liter four-opening flask equipped with a stirrer, a thermometer, a dropping funnel and a reflux condenser, 553 g (4.0 mol) of bicyclo(2,2,1)hept-5-ene-2 carboxylic acid and 425 g (4.82 mol) of t-pentyl alcohol, and 165.6 g of N,N-dimethylacetamide were prepared. After replacing gas inside the flask with nitrogen gas, the temperature was raised to 60° C. and the starting materials were stirred and dissolved.

While maintaining the same temperature, a solution, in which 915.4 g (4.8 mol) of p-toluenesulfonylchloride was dissolved in 915 g of pyridine, was added drop by drop for 4 hours, and then this mixture was stirred at the same temperature for a night. After the reaction was complete, 1660 g of water was added to the reaction mixture obtained. After stirring it, a water layer was removed by separating the mixture into two liquids.

600 g of a 16% NaOH aqueous solution was added to a remaining oil layer. After stirring it by further adding water, the water layer was removed by separating it into two liquids. By vacuum distillation of an oil layer obtained, the target compound, 709 g of bicyclo(2,2,1)hept-5-ene-2-carboxylic acid-t-pentyl ester, was obtained as an a chromic transparent liquid with 99.1% purity (by gas chromatography analysis). (A yield ratio of the target compound to the raw material carboxylic acid was 85.3%.)

[Embodiment 5]
Producing Norbornane Carboxylic Acid-adamanthyl Ester [Chemical Formula 8]

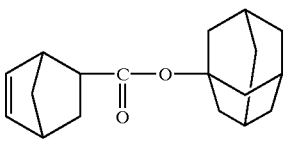

(8)

In a 1-liter four-opening flask equipped with a stirrer, a thermometer, a dropping funnel and a reflux condenser, 3.9 g (0.028 mol) of bicyclo(2,2,1)hept-5-ene-2 carboxylic acid and 4.5 g (0.0296 mol) of 1-adamantanol and 1.2 g of N,N-dimethylacetamide, and 6.6 g of pyridine were prepared. After replacing gas inside the flask with nitrogen gas, the temperature was raised to 60° C. and the starting materials were stirred and dissolved.

While maintaining the same temperature, a solution, in which 5.6 g (0.0294 mol) of p-toluenesulfonylchloride was dissolved in 6.6 g of pyridine, was added drop by drop for 1.5 hours, and then this mixture was stirred at the same temperature for a night. After the reaction was complete, 30 g of toluene and 30 g of water were added to the reaction mixture obtained. After stirring it, a water layer was removed by separating the mixture into two liquids.

2.1 g of a 16% NaOH aqueous solution was added to a remaining oil layer. After stirring it upon further adding water, the water layer was removed by separating it into two liquids. By removing toluene, etc. contained in an oil layer obtained by vacuum distillation and crystallizing a residue by methanol, the target compound, 5.3 g of bicyclo(2,2,1)hept-5-ene-2-carboxylic acid-1-adamanthyl ester, was obtained as a white crystal with 92.3% purity (by liquid chromatography analysis). (A yield ratio of the target compound to the raw material carboxylic acid was 64.4%.)

[Embodiment 6]
Producing Benzoic Acid t-butyl Ester

In a 1-liter four-opening flask equipped with a stirrer, a thermometer, a dropping funnel and a reflux condenser, 12.2 g (0.1 mol) of benzoic acid and 8.9 g (0.12 mol) of t-butyl alcohol and 3.7 g of N,N-dimethylacetamide were prepared. After replacing gas inside the flask with nitrogen gas, the temperature was raised to 60° C. and the starting materials were stirred and dissolved.

While maintaining the same temperature, a solution, in which 22.9 g (0.12 mol) of p-toluenesulfonylchloride was dissolved in 22.2 g of pyridine, was added drop by drop for one hour, and then this mixture was stirred at the same temperature for two hours. After the reaction was complete, 50 g of water was added to the reaction mixture obtained. After stirring it, a water layer was removed by separating the mixture into two liquids.

12 g of a 16% NaOH aqueous solution was added to the remaining oil layer. After stirring it upon further adding water, the water layer was removed by separating it into two liquids. By vacuum distilling an oil layer obtained and crystallizing a residue by methanol, the target compound, 13.3 g of benzoic acid t-butyl ester, was obtained as a white crystal with 98.7% purity (by gas chromatography analysis). (A yield ratio of the target compound to the raw material benzoic acid was 74.9%.)

[Embodiment 7]

Producing Propionic Acid t-butyl Ester

In a 1-liter four-opening flask equipped with a stirrer, a thermometer, a dropping funnel and a reflux condenser, 7.4 g (0.1 mol) of propionic acid and 8.9 g (0.12 mol) of t-butyl alcohol and 2.2 g of N,N-dimethylacetamide were prepared. After replacing gas inside the flask with nitrogen gas, the temperature was raised to 60° C. and the starting materials were stirred and dissolved.

While maintaining the same temperature, a solution, in which 22.9 g (0.12 mol) of p-toluenesulfonylchloride was dissolved in 22.2 g of pyridine, was added drop by drop for one hour, and then this mixture was stirred at the same temperature for two hours. After the reaction was complete, 50 g of water was added to the reaction mixture obtained. After stirring it, a water layer was removed by separating the mixture into two liquids.

12 g of a 16% NaOH aqueous solution added to the remaining oil layer. After stirring it upon further adding water and 4.4% hydrochloric acid water, the water layer was removed by separating it into two liquids. By vacuum distilling an oil layer obtained after further rinsing a remaining oil layer and separating it into tow liquids, the target compound, 6.1 g of propionic acid t-butyl ester, was obtained as a transparent liquid with 99.9% purity (by gas chromatography analysis). (A yield ratio of the target compound to the raw material propionic acid was 46.9%.)

[Embodiment 8]

Producing Decahydronaphthalene-2,6-dicarboxylic Acid di-t-butyl Ester [Chemical Formula 9]

(9)

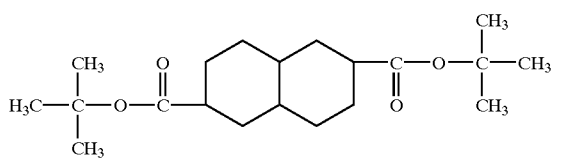

In a 1-liter four-opening flask equipped with a stirrer, a thermometer, a dropping funnel and a reflux condenser, 113 g (0.5 mol) of decahydronaphthalene-2,6-dicarboxylic acid and 88.8 g (1.2 mol) of t-butanol, and 34 g of N,N-dimethylacetamide were prepared. After replacing gas inside the flask with nitrogen gas, the temperature was raised to 60° C. and the starting materials were stirred and dissolved.

While maintaining the same temperature, a solution, in which 228.8 g (1.2 mol) of p-toluenesulfonylchloride was dissolved in 237 g of pyridine, was added drop by drop for four hours, and then this mixture was stirred at the same temperature for a night. After the reaction was complete, 300 g of toluene and 300 g of water were added to the reaction mixture obtained. After stirring it, a water layer was removed by separating the mixture into two liquids.

75 g of a 16% NaOH aqueous solution was added to the remaining oil layer. After stirring it upon further adding water, the water layer was removed by separating it into two liquids. By vacuum distilling toluene, etc. contained in an oil layer obtained and crystallizing a residue by methanol, the target compound, 80.2 g of decahydronaphthalene-2,6-dicarboxylic acid di-t-butyl ester, was obtained as a white crystal with 100% purity (by gas chromatography analysis). (A yield ratio of the target compound to the raw material carboxylic acid was 47.5%.)

According to the production method according to the present invention, various types of carboxylic acid tertiary alkyl esters can be produced from starting materials, carboxylic acid and tertiary alcohol, in a single-step reaction process which can be implemented on an industrial scale.

Both raw materials and products are thermally stable compounds. Reaction conditions are moderate, which do not generate pyrolysis. Using this method, carboxylic acid tertiary alkyl esters can be easily produced on an industrial scale at high purity and a high yield ratio.

What is claimed is:

1. A method for producing a carboxylic acid tertiary alkyl ester of chemical formula 1, comprising continually adding an esterification agent possessing a monovalent acid group, which agent is ester-interchangeable with a tertiary alcohol, to a mixed fluid of a carboxylic acid and a tertiary alcohol in the presence of a compound comprising a tertiary amide group as a catalyst:

$$R_1(COOR_2)_n \quad (1)$$

wherein $R_1$ represents a hydrocarbon group; $R_2$ is a tertiary saturated hydrocarbon group; n is a integer of 1 or 2.

2. The method for producing a carboxylic acid tertiary alkyl ester as claimed in claim 1, wherein the esterification agent possessing a monovalent acid group and being ester-interchangeable with a tertiary alcohol is an aromatic sulfonyl halogenide of chemical formula 2:

$$X\text{---}SO_2Ar \quad (2)$$

wherein X is a halogen atom; Ar is a benzene ring or an alkyl-substituted benzene ring of one to three carbons.

3. The method for producing a carboxylic acid tertiary alkyl ester as claimed in claim 1, wherein a base coexist.

4. The method for producing a carboxylic acid tertiary alkyl ester as claimed in claim 1, wherein the carboxylic acid is a monocarboxylic acid or a dicarboxylic acid.

* * * * *